United States Patent [19]

Hitzman et al.

[11] E Re. 30,543

[45] Reissued Mar. 10, 1981

[54] **METHANOL FOAM FERMENTATION TO SINGLE CELL PROTEIN BY *PSEUDOMONAS METHANICA***

[75] Inventors: Donald O. Hitzman; Eugene H. Wegner, both of Bartlesville, Okla.

[73] Assignee: Provesta Corporation, Bartlesville, Okla.

[21] Appl. No.: 761,171

[22] Filed: Jan. 21, 1977

Related U.S. Patent Documents

Reissue of:

[64] Patent No.: 3,982,998
Issued: Sep. 28, 1976
Appl. No.: 530,422
Filed: Dec. 6, 1974

[51] Int. Cl.[3] ..... C12N 1/34; C12N 1/20

[52] U.S. Cl. ..... 435/246; 435/247; 435/253; 435/254; 435/255

[58] Field of Search ..... 195/49, 107, 108, 109, 195/115, 142, 143, 144; 435/246, 247, 253, 254, 255, 315

[56] References Cited

U.S. PATENT DOCUMENTS

| | | | |
|---|---|---|---|
| 2,983,652 | 5/1961 | Baerfuss . | |
| 3,677,895 | 7/1972 | Hashimoto | 195/107 |
| 3,705,082 | 12/1972 | Hondermark et al. | 195/107 |
| 3,755,082 | 8/1973 | Terui et al. | 195/49 |
| 3,764,481 | 10/1973 | Muller et al. | 195/109 |
| 3,847,750 | 11/1974 | Ridgway et al. | 435/315 |
| 3,926,737 | 12/1975 | Wilson et al. | 195/117 X |

FOREIGN PATENT DOCUMENTS

| | | | |
|---|---|---|---|
| 681847 | 10/1939 | Fed. Rep. of Germany | 195/109 |
| 682520 | 10/1939 | Fed. Rep. of Germany | 195/109 |
| 2006235 | 12/1969 | France | 195/49 |
| 1210770 | 10/1970 | United Kingdom | 195/49 |

OTHER PUBLICATIONS

Oki et al, "New Yeast Capable of Assimilating Methanol", *J. Gen. Appl. Microbiol.*, vol. 18, pp. 295–305 (1972).

Cooney et al., "Microbial Utilization of Methanol", *App. Microb.*, vol. 15 (1972) pp. 337–365.

Einsole, "Der Einfluss von Ruhren und Mischen in Reaktoren auf Mikrobiologische Fliesskulturen", *Chemische Rundschau*, vol. 26, No. 16 (1973).

Lodder et al., *The Yeasts*, North-Holland Publishing Co., Amsterdam, London, (1970) pp. 296–299.

*Primary Examiner*—Thomas G. Wiseman

[57] ABSTRACT

A process for the production of microbial cells by fermenting a carbonaceous material in a foam fermenter containing an oxygen-enriched nutrient medium. The process uses a source of carbon which is assimilable by the microorganism for the production of the microbial cells. The microbial cells are separated and removed from the foam fermenter for use as a food product high in protein content.

2 Claims, 1 Drawing Figure

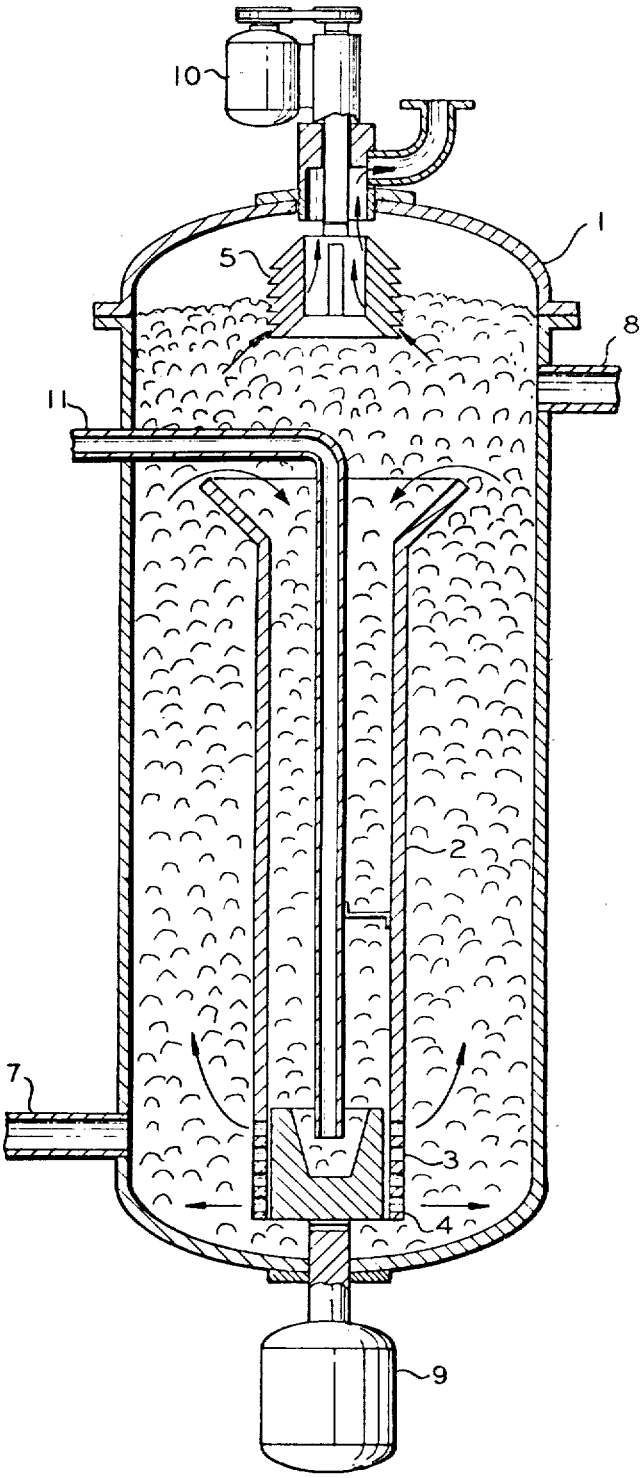
10
1
5
8
11
2
7
3
4
9

METHANOL FOAM FERMENTATION TO SINGLE CELL PROTEIN BY *PSEUDOMONAS METHANICA*

Matter enclosed in heavy brackets [ ] appears in the original patent but forms no part of this reissue specification; matter printed in italics indicates the additions made by reissue.

*This is a reissue application of U.S. Pat. application Ser. No. 530,422, filed Dec. 6, 1974, now U.S. Pat. No. 3,982,998.*

The present invention relates to a process for the propagation of microbial cells and in one aspect is directed to a process for the propagation of alcohol assimilating microbial cells by the aerobic culturing of a suitable microorganism which can assimilate alcohol as the main source of carbon. Current world-wide food shortages have encouraged the research and development of methods of producing high quality, low cost microbial protein, i.e., single cell protein to alleviate the food shortages. Considerable development work in such fermentation processes has been directed toward the use of hydrocarbons and other carbonaceous materials which would normally be flared or otherwise disposed of in petroleum refining. The use of methanol as the main source of carbon has been particularly attractive because of the advantages offered thereby. Such advantages include: methanol is miscible with water, is easily and cheaply produced from a wide range of hydrocarbon materials, can be easily produced in virtually any area of the world having any form of fossil fuel supplies, is characterized by the absence of potentially carcinogenic polycyclic hydrocarbons, etc.

The present invenion can be regarded as a process of aerobically fermenting a carbon source assimilable by a microorganism in fermenters which operate under essentially foam-filled conditions. In one aspect, the carbon source is an alcohol which is assimilated by a suitable microorganism for the production of microbial cells which can be used as a food source (single cell protein). It has been found that fermentation carried out in a foam-filled fermenter in certain fermentation processes is highly efficient when carried out in a continuous process. The foamed contents of the fermenter can be described as the dispersion of the gaseous phase within the liquid phase or occasionally may be described as an emulsified gaseous phase or simply as an emulsion of the gaseous and liquid phases wherein increased surface area contact is effected between the gas and liquid phases for enhancing the fermentation process. Specifically, it has been found that the fermentation productivity (grams of cells per liter of mixture per hour) is significantly higher when using the foam fermenter than when a conventional paddle stirred tank fermenter is employed.

Fermentation vessels suitable for the formation and maintenance of the contents in a foamed state are known in the fermentation art. Generally, such vessels are those which provide vigorous agitation to the contents with concomitant introduction of some free oxygen-containing substances such as air to the mixture. In carrying out the process, small amounts of surfactants can also be employed to aid in the formation and maintenance of the foam. However, this is not usually required since it is known that many microbial growth processes involve the formation of materials (cellular or extracellular) which have surfactant properties and thus induce foaming. In fact, in some fermentation processes it is often necessary to resort to the use of antifoam agents to control the degree of foaming during the fermentation process.

Therefore, the principal objects of the present invention are: to provide a process for fermentation of a carbonaceous substance to effect growth of microbial cells for the production of an edible food product such as single cell protein; to provide such a process which involves the use of a foam-filled fermenter using methanol as the assimilable carbon source; to provide such a process which can be used with numerous types of microorganisms including those in the classes of bacteria, fungi and yeast for the production of single cell protein; and to provide such a process which is efficient and well adapted for its intended use.

Other objects and advantages of the present invention will become apparent from the following detailed description taken in connection with the accompanying drawings wherein are set forth by way of illustration and example certain embodiments of the present invention.

FIG. 1 is a schematic representation of a fermenter used in the practice of foam fermenting processes.

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting but merely as a basis for the claims and as a representative basis for teaching one skilled in the art to variously employ the present invention in virtually any appropriate manner.

Referring more in detail to the drawing:

FIG. 1 shows a typical fermentation reactor, as is known in the art, which is comprised of a housing 1 having a hollow interior. A draft tube 2 is positioned within the housing 1 and provides a flow path for the medium contained within the housing 1 to help induce circulation. At the lower end of the draft tube 2 there is a pump such as a turbine 3 which helps induce flow downwardly through the draft tube 2 and through emulsifying sieves 4 to the exterior of the draft tube 2 and upwardly therefrom. Positioned adjacent to the top of the housing 1 there is provided a foam breaker 5 which is operable to break foam which accumulates in the upper portion of the housing 1. An outlet 7 is provided adjacent to the lower portion of the housing 1 to draw off a portion of the contents for further processing. The outlet 7 preferably is a conduit which connects the lower portion of the housing 1 to secondary processing equipment (not shown). An inlet 8 is provided adjacent to the upper portion of the housing 1 and is adapted for the delivery of portions of the medium used in the fermentation process. Power means such as motors 9 and 10 are operably connected to the turbine 4 and foam breaker 5, respectively, for power operation thereof. A conduit 11 is in communication with the interior of the housing 1 and is adapted for the introduction of a source of oxygen, such as air, into the medium.

In a preferred embodiment of this invention, the fermentation is carried out with a straight chain alcohol having from 1 to 16 carbon atoms per molecule. This is referred to as the feedstock and is assimilable by the microorganism and supplies the carbon and energy for the microbial growth. Preferably the alcohol has from 1 to 6 carbon atoms per molecule and more preferably the alcohol will be either ethanol or methanol and most preferably, methanol. Examples of suitable alcohols include methanol, ethanol, 1-propanol, 1-butanol, 1-octanol, 1-dodecanol, 1-hexadecanol, 2-propanol, 2-butanol, 2-hexanol and the like. Mixtures of alcohols can also be employed if desired.

The microorganism used in the fermentation process is capable of assimilating one or more of the above alcohols as the source of carbon and energy in the growth or propagation of the microorganism. Suitable microorganism can be selected from bacteria, yeast and fungi.

Suitable yeasts include species from the genera Candida, Hansenula, Torulopsis, Saccharomyces, Pichia, Debaryomyces, Lipomyces, Cryptococcus, Nematospora, and Brettanomyces. The preferred genera include Candida, Hansenula, Torulopsis, Pichia, and Saccharomyces. Examples of suitable species include:

Candida boidinii
Candida mycoderma
Candida utilis
Candida stellatoidea
Candida robusta
Candida claussenii
Candida rugosa
Brettanomyces petrophilium
Hansenula minuta
Hansenula saturnus
Hansenula californica
Hansenula mrakii
Hansenula silvicola
Hansenula polymorpha
Hansenula wickerhamii
Hansenula capsulata
Hansenula glucozyma
Hansenula henricii
Hansenula nonfermentans
Hansenula philodendra
Torulopsis candida
Torulopsis bolmii
Torulopsis versatilis
Torulopsis glabrata
Torulopsis molishiana
Torulopsis nemodendra
Torulopsis nitratophila
Torulopsis pinus
Pichia farinosa
Pichia polymorpha
Pichia membranaefaciens
Pichia pinus
Pichia pastoris
Pichia trehalophila
Saccharomyces cerevisiae
Saccharomyces fragilis
Saccharomyces rosei
Saccharomyces acidifaciens
Saccharomyces elegans
Saccharomyces rouxii
Saccharomyces lactis
Saccharomyces fractum Suitable bacteria include species from the genera Bacillus, Mycobacterium, Actinomyces, Nocardia, Pseudomonas, Methanomonas, Protaminobacter, Methylococcus, Arthrobacter, Methylomonas, Brevibacterium, Acetobacter, Micrococcus, Rhodopseudomonas, Corynebacterium, Rhodopseudomonas, Microbacterium, Achromobacter, Methylobacter, Methylosinus, and Methylocystis. Preferred genera include Bacillus, Pseudomonas, Protaminobacter, Micrococcus, Arthrobacter and Corynebacterium.

Examples of suitable species include:

Bacillus subtilus
Bacillus cereus
Bacillus aureus
Bacillus acidi
Bacillus urici
Bacillus coagulans
Bacillus mycoides
Bacillus circulans
Bacillus megaterium
Bacillus licheniformis
Pseudomonas methanolica
Pseudomonas ligustri
Pseudomonas orvilla
Pseudomonas methanica
Pseudomonas fluorescens
Pseudomonas aeruginosa
Pseudomonas oleovorans
Pseudomonas putida
Pseudomonas boreopolis
Pseudomonas pyocyanea
Pseudomonas methylphilus
Pseudomonas brevis
Pseudomonas acidovorans
Pseudomonas methanoloxidans
Pseudomonas aerogenes
Protaminobacter ruber
Corynebacterium simplex
Corynebacterium hydrocarbooxydans
Corynebacterium alkanum
Corynebacterium oleophilus
Corynebacterium hydrocarboclastus
Corynebacterium glutamicum
Corynebacterium viscosus
Corynebacterium dioxydans
Corynebacterium alkanum
Micrococcus cerificans
Micrococcus rhodius
Arthrobacter rufescens
Arthrobacter parafficum
Arthrobacter simplex
Arthrobacter citreus
Methanomonas methanica
Methanomonas methanooxidans
Methylomonas agile
Methylomonas albus
Methylomonas rubrum
Methylomonas methanolica
Mycobacterium rhodochrous
Mycobacterium phlei
Mycobacterium brevicale
Nocardia salmonicolor
Nocardia minimus
Nocardia corallina
Nocardia butanica
Rhodopseudomonas capsulatus
Microbacterium ammoniaphilum
Archromobacter coagulans
Brevibacterium butanicum
Brevibacterium roseum
Brevibacterium flavum
Brevibacterium lactofermentum
Brevibacterium paraffinolyticum
Brevibacterium ketoglutamicum
Brevibacterium insectiphilium Suitable fungi include species from the genera Aspergillus, Monilia, Rhizopus, Penicillium, Mucor, Alternaria and Helminthosporium.

Examples of suitable species of fungi include:

Aspergillus niger
Aspergillus glaucus
Aspergillus flavus
Aspergillus terreus
Aspergillus itconicus
Penicillium notatum
Penicillium chrysogenum
Penicillum glaucum
Penicillium griseofulvum
Penicillium expansum
Penicillium digitatum
Penicillium italicum
Rhizopus nigricans
Rhizopus oryzae
Rhizopus delemar
Rhizopus arrhizus
Rhizopus stolonifer
Mucor mucedo
Mucor genevensis The growth of the microorganism is sensitive to the operating temperature of the fermenter and each particular microorganism has an optimum temperature for growth. The broad temperature range employed for the fermentation process of this invention would be from about 30° C. to 65° C. and more preferably between 35° and 60° C. The temperature selected will generally depend upon the microorganism employed in the process since they will have a somewhat different temperature/growth rate relationship.

In the practice of the present invention, a suitable nutrient medium is supplied to the fermenter to provide nutrients such as an assimilable source of nitrogen, phosphorus, magnesium, calcium, potassium, sulfur and sodium as well as trace quantities of copper, manganese, molybdenum, zinc, iron, boron, iodine and selenium. As is well known in the art of fermentation, the relative amounts of the above nutrients can vary depending on the microorganism selected for the process. In addition, the nutrient medium can also contain vitamins as is known in the art when their presence is known to be desirable for the propagation of certain microorganisms. For example, many yeasts appear to require the presence of one or both of the vitamins, biotin and thiamin for their proper propagation. A typical example of a suitable nutrient medium is as follows:

| One Liter Aqueous Solution | |
|---|---|
| Component | Amount |
| $H_2PO_4$ (85%) | 2.0 ml |
| KCl | 1.0 g |
| $MgSO_4$ $7H_2O$ | 1.5 g |
| $CaCl_2$ $2H_2O$ | 0.2 g |
| NaCl | 0.1 g |
| Trace Mineral Solution | 5.0 ml |

The trace mineral solution as listed in the above recipe is formulated as given in the recipe below:

| One Liter Aqueous Solution (Trace Mineral Solution) | |
|---|---|
| Component | Amount |
| $CuSO_4$ $5H_2O$ | 0.06 g |
| KI | 0.08 g |

-continued

| One Liter Aqueous Solution (Trace Mineral Solution) | |
|---|---|
| Component | Amount |
| $FeCl_3$ $6H_2O$ | 4.80 g |
| $MnSO_4$ $H_2O$ | 0.30 g |
| $Na_2MoO_4$ $2H_2O$ | 0.20 g |
| $ZnSO_4$ $7H_2O$ | 2.00 g |
| $H_3BO_2$ | 0.02 g |

When using the nutrient medium described above the source of assimilable nitrogen is supplied by the separate addition of aqueous ammonia ($NH_4OH$) to the fermentation vessel. The amount of $NH_4OH$ added will depend upon the pH desired for the reaction mixture. Without any added $NH_4OH$ the pH will be about 2, for the nutrient medium. Preferably for the utilization of yeasts or fungi in the fermentation process the pH is preferably in the range of approximately 3–5 and for the utilization of bacteria the pH should preferably be in the range of approximately 6–7.5.

The fermentation reaction is an aerobic process wherein the oxygen needed for the process can be supplied from a free oxygen-containing source such as air which is suitably supplied to the fermentation vessel at a pressure of from approximately 1–100 atmospheres and preferably from 1–10 atmospheres. One good source of oxygen is oxygen enriched air. The fermentation reaction is often favorably affected by use of pressure within the above-described broad and preferred ranges.

Preferably the fermentation process of the instant invention is a continuous type but it is to be noted that it can be conducted as a batch process. In the continuous or batch process modes of operation the fermentation reactor is first sterilized and subsequently inoculated with a culture of the desired microorganism in the presence of all the required nutrients including oxygen and the carbon source. In the continuous method of operation the oxygen source or air is continuously introduced along with continuous introduction of nutrient medium, nitrogen source (if added separately) and alcohol at a rate which is either predetermined or in response to need which can be determined by monitoring such things as alcohol concentration, dissolved oxygen, and oxygen or carbon dioxide in the gaseous effluent from the fermenter. The feed rate of the various materials can be varied so as to obtain as rapid a cell growth as possible consistent with efficient utilization of the alcohol feed, i.e., a high yield of cell weight per weight of alcohol feed charged.

As is known in the art, the feed rate of the alcohol is an important variable to control since in high concentration this material can actually inhibit cell growth and may even kill the microorganism. Therefore, the feed rate of the alcohol is adjusted such that the alcohol is consumed by the microorganism at essentially the same rate as it is being fed to the fermenter. When this condition is attained there will be, of course, little or no alcohol in the effluent which is continuously withdrawn from the fermenter in a continuous type of process. However, satisfactory operation can be achieved with up to about 0.5 percent by volume alcohol concentration in the effluent. For high cell productivity or growth rate, the concentration of alcohol in the feed to the fermenter should be from about 7 percent up to about 30 percent by volume.

For batch or continuous operation of the process of this invention, the concentration of feedstock, e.g., methanol, in the fermenter should be within the range of from 0.001 up to 5 percent (v/v) and preferably from 0.005 up to 0.5 percent (v/v). It is possible, of course, and may in some instances be desirable, to add the feedstock incrementally to an otherwise typical batch fermentation process.

It is well known in the art that instrumentation is available to measure cell density, pH, dissolved oxygen and alcohol concentration in the fermenter as well as the feed and effluent streams so as to provide a rather complete monitoring of the fermentation process with the instrumentation being adapted to control the input rates so as to optimize the process. The materials fed to the fermenter are preferably subjected to sterilization as is normally done in the art in order to prevent contamination of the desired fermentation mixture by unwanted viable microorganisms.

The effluent removed from the fermentation vessel is suitably treated for separating the microbial cells, containing single cell protein, therefrom. The usual method of treatment is well known to those in the art and employs the use of heat and/or chemical reagents, e.g., acids, to kill the microbial cells and aid in their separation from the aqueous phase by coagulation or flocculation of the cells. After this treatment the mixture is next centrifuged to remove most of the liquid phase and then the separated cells are further dried such as by drum dryers or spray dryers. If yeast is used as the culture the above sequence of steps can be modified by first centrifuging the effluent to separate the cells which are then killed by heat prior to or during a later drying step. After separation and drying, the cells which contain a high amount of protein are then ready or available for use as a food source by animals and/or humans.

The single cell protein produced by the above process has a particularly important utility in the world today. As has been increasingly emphasized in recent years, the supply of abundant and inexpensive protein available for human or animal consumption such as fishmeal and soya bean meal is being strained by an ever-increasing world population and recent reduction in production of certain types of protein as, for example, fishmeal based on anchovy fishing harvests. The production of single cell protein (SCP) offers a way to alleviate this situation by providing a source of protein suitable for inclusion in the diets of poultry, swine, cattle which directly or indirectly provide protein for humans. The microbial cells produced according to the above process are suitable single cell protein sources and can thus be employed for food purposes. It is known that the protein produced by this process can be employed in other areas such as the production of proteinaceous adhesive compositions and the like. The following are typical examples of the above process.

EXAMPLE I

Three fermentation runs were conducted with methanol as the carbon and energy source in a fermenter operating under essentially foam-filled conditions. Said fermenter was of the general type described above. The volume of said fermenter was about 1500 liters. In each run the temperature was maintained at 39° C. and the pH at 6.6. In each run essentially no methanol was detected in the fermenter effluent and the methanol concentration in the feed was 10 percent by volume. The nutrient medium employed in these runs was that previously described. The microorganism employed in each of these runs was a bacteria characterized as a Pseudomonas species and was Pseudomonas methanica as identified by the depository number NRRL B3449. The data presented in Table I below was taken after each run had reached essentially steady state operation (after about 12 hours continuous operation). The runs were carried out at three different pressures as shown in the table.

TABLE I

| | Run No. | | |
|---|---|---|---|
| | 1 | 2 | 3 |
| Pressure atmospheres | 1 | 1.97 | 2.6 |
| Fermenter charge. kg | 830 | 810 | 750 |
| Air flow. $m^3$/hr | 164 | 125[a] | 68.5[b] |
| Dissolved $O_2$ in fermenter, %[c] | 48 | 55 | 15 |
| $O_2$ Level in exhaust air, %[d] | 78 | 67 | 40 |
| Medium feed rate, l/hr | 145 | 235 | 270 |
| $NH_4OH$ (25%) feed rate[e] l/hr | 0.8 | 2.3 | 4 |
| Dry cell wt. g/l | 22.7[f] | 30.6[g] | 24.6[f] |
| Fermenter stirrer, rpm | 1110 | 950 | 940 |
| Calculated Values | | | |
| Dilution rate, $hr^{-1}$ | 0.175 | 0.29 | 0.36 |
| Retention time, hr. | 5.7 | 3.44 | 2.8 |
| Aeration rate/ V/V/min | 3.3 | 2.5 | 1.5 |
| $O_2$ Consumed, kg/kg cells | 3.6 | 2.3 | 3.3 |
| Cell yield, kg$CH_3OH$[h]/kg cells | 3.48 | 2.58 | 3.21 |
| Crude protein, %[i] | 75 | 75 | 75 |
| Productivity, g cells/l/hr | 4.0 | 8.9 | 8.8 |

[a]At 2 atmospheres inlet pressure.
[b]At 2.75 atmospheres inlet pressure.
[c]Based on dissolved $O_2$ content with no cells present.
[d]Based on normal $O_2$ content of air.
[e]Approximate values of $NH_4OH$ (25% by wt $NH_3$) consumption.
[f]Cells isolated by filtration of a sample through a Millipore filter.
[g]Cells isolated by centrifuging at 10 cc sample, washing cells, recentrifuging, drying, and weighing cells.
[h]Based on methanol consumed.
[i]Nitrogen content of cells by Kjeldahl analysis X 6.25.

The results of these runs demonstrate the excellent productivity results of the continuous fermentation process using an essentially foam filled fermenter with oxygen transfer capabilities of about 1000 mmole $O_2$ per liter per hour of liquid fermentation reaction mixture.

EXAMPLE II (Control)

A continuous fermentation run (4) was also carried out using the same bacteria culture, nutrient medium, and methanol concentration in the feed as the runs of Example I. The temperature (40° C.) and pH (6.3) were also very close to the same values used in the runs of Example I. However, this run employed a conventional large tank equipped with a simple blade stirrer as the fermentation vessel operated at atmospheric pressure. Volume of the fermentation mixture was about 1125 liters. No methanol was detected in the fermenter effluent. A dry cell weight of 19.1 g/l was obtained in this run. Other calculated results are presented below for this run:

| | |
|---|---|
| Dilution rate, hr 1 | 0.12 |
| Retention time, hr | 8.3 |
| Yield, kg$CH_3OH$/kg cells | 4.0 |
| Crude protein, % | 75 |
| Productivity, g/l/hr | 2.3 |

The productivity results from this run are clearly inferior to those of Run 1 of Example I, a comparable run using the foam-filled fermenter.

EXAMPLE III

Two other continuous methanol fermentation runs were carried out using the foam-filled fermenter employed in Example I and using the same nutrient medium as in Example I but with a yeast culture identified as Hansenula polymorpha.

These runs employed a 10 percent by volume methanol concentration in the feed and no methanol was detected in the effluent from the fermenter. Each run was conducted at atmospheric pressure.

During the course of Run 5 it was discovered that the fermentation mixture had become contaminated with a filamentous fungi. This contamination was not believed to have had a significant effect on the operating data for the run but the reactor system was sterilized before Run 6 which ran with no apparent contamination.

Data from Runs 5 and 6 are presented in Table II below. The data shown are considered typical for the continuous fermentation of methanol under the conditions shown.

TABLE II

| | Run No. | |
|---|---|---|
| | 5 | 6 |
| Fermenter charge, kg | 800 | 725 |
| Temperature, °C. | 38 | 39 |
| Air flow, $m^3$/hr | 101 | 121 |
| Dissolved $O_2$ in fermenter, %[a] | 24 | —[b] |
| $O_2$ Level in exhaust air, % | —[b] | 84 |
| pH | 3.5 | 3.6 |
| Medium feed rate, l/hr | 112 | 86 |
| $NH_4OH$(25%) feed rate[c], l/hr | —[b] | 1 |
| Dry cell wt. g/l | 26 | 24 |
| Fermenter stirrer, rpm | 1000 | 980 |
| Calculated Values | | |
| Dilution rate, $hr^{-1}$ | 0.14 | 0.12 |
| Retention time, hr | 7.2 | 8.4 |
| Aeration rate, V/V/min | 2.1 | 2.8 |
| $O_2$ Consumed, kg/kg cells | 3 | 3.4 |
| Cell yield, kg $CH_3OH$[d]/kg cells | 3.04 | 3.29 |
| Crude protein, %[e] | 54 | 54 |
| Productivity, g/l/hr | 3.6 | 2.9 |

[a]See footnote [c] Table I.
[b]Not determined.
[c]See footnote [e] Table I.
[d]See footnote [b] Table I.
[e]See footnote [i] Table I.

These results demonstrate the use of a yeast for the continuous fermentation of methanol in a foam-filled fermenter to produce single cell protein.

Since yeast has an inherently slower growth rate than bacteria, the productivity shown in Table II is lower than was obtained when using bacteria.

It is to be understood that while we have illustrated and described certain forms of our invention it is not to be limited to the specific form of the invention disclosed herein:

We claim:

[1. A process for the production of microbial cells, said process including the steps of:

a. placing a microorganism into a fermenter containing a nutrient medium and aerobically culturing said microorganism, said microorganism being capable of assimilating alcohol as a main source of carbon;

b. introducing an alcohol having from 1–16 carbon atoms into said fermenter as the main carbon source for said microorganism to assimilate and produce microbial cells;

c. maintaining said alcohol and medium in a foamed condition in said fermenter so that said fermenter is essentially foam-filled; and d. separating and recovering the microbial cells produced in said fermenter.]

[2. The process as set forth in claim 1 wherein:

a. said alcohol has from 1–6 carbon atoms.]

[3. The process as set forth in claim 1 wherein:

a. said alcohol is methanol.]

[4. The process as set forth in claim 3 wherein:

a. said microorganism is Pseudomonas methanica.]

[5. The process as set forth in claim 4 wherein:

a. said microorganism is Pseudomonas methanica NRRL B3449.]

[6. The process as set forth in claim 3 wherein:

a. said methanol is present in the fermenter in the range of approximately 0.001 to 5% by volume of the contents.]

[7. The process as set forth in claim 6 wherein:

a. said methanol is introduced at a rate wherein a minimum of methanol is discharged from the fermenter with effluent normally discharged from the fermenter.]

[8. The process as set forth in claim 3 wherein:

a. said microorganism is Hansenula polymorpha.]

[9. The process as set forth in claim 3 wherein:

a. said fermenter is maintained during operation at a pressure above 1 atmosphere.]

[10. The process as set forth in claim 3 wherein:

a. said fermenter is operated at a temperature between approximately 30° to 65° C.]

[11. The process as set forth in claim 3 wherein:

a. said process is continuous wherein oxygen and said nutrient and methanol are continuously introduced into said fermenter at controlled rates.]

[12. A process for the production of microbial cells, said process including the steps of:

a. placing a microorganism in a fermenter, said microorganism being capable of assimilating a straight chain alcohol having 1 to 16 carbon atoms per molecule as a main source of carbon;

b. continuously introducing a nutrient medium into said fermenter at a controlled rate;

c. introducing oxygen into said fermenter continuously at a controlled rate for aerobically fermenting said alcohol;

d. continuously introducing said alcohol into said fermenter at a controlled rate for said microorganism to assimilate as the carbon source and produce microbial cells;

e. maintaining said fermenter during operation at a pressure of at least approximately 1 atmosphere;

f. maintaining said alcohol and medium in a foamed condition in said fermenter so that said fermenter is essentially foam-filled; and g. continuously separating and recovering the microbial cells produced in said fermenter.]

[13. The process as set forth in claim 12 wherein:

a. said microorganism is Pseudomonas methanica.]

[14. The process as set forth in claim 13 wherein:

a. said alcohol is present in the fermenter in the range of approximately 0.001 to 5% by volume of the contents;

b. maintaining said fermenter at an operating temperature of approximately 30° to 65° C.]

[15. The process set forth in claim 12 wherein:

a. said microorganism is Hansenula polymorpha.]

[16. The process as set forth in claim 12 wherein:

a. said alcohol is methanol.]

*17. A process for production of microbial cells in a fermentation vessel having a draft tube positioned therein with a first flow path portion through said draft tube and a second flow portion between the draft tube and a portion of the vessel, said process including the steps of:*

*(a) placing a microorganism into a fermenter vessel containing an aqueous nutrient medium and aerobically culturing said microorganism, said microorganism being capable of assimilating alcohol as a main source of carbon;*

*(b) introducing oxygen into the fermenter;*

*(c) introducing at least one alcohol selected from the group consisting of methanol and ethanol into the fermenter vessel as the main carbon source for said microorganism to assimilate and produce microbial cells;*

*(d) maintaining said alcohol and medium in a foamed condition in said fermenter vessel so that said fermenter vessel is essentially foam-filled;*

*(e) continuously circulating the foamed alcohol and medium through the first flow path portion to the second flow path portion and then back to the first flow path portion within the fermenter in loop flow; and*

*(f) separating and recovering the microbial cells produced in said fermenter vessel;*

*wherein said microorganism is Pseudomonas methanica.*

*18. The process as set forth in claim 17 wherein:*

*a. said microorganism is Pseudomonas methanica NRRL B3449.*

* * * * *